United States Patent [19]

Frid

[11] Patent Number: 5,741,333
[45] Date of Patent: Apr. 21, 1998

[54] SELF-EXPANDING STENT FOR A MEDICAL DEVICE TO BE INTRODUCED INTO A CAVITY OF A BODY

[75] Inventor: Noureddine Frid, Beersel, Belgium

[73] Assignee: Corvita Corporation, Miami, Fla.

[21] Appl. No.: 626,933

[22] Filed: Apr. 3, 1996

[30] Foreign Application Priority Data

Apr. 12, 1995 [BE] Belgium ................ 09500335

[51] Int. Cl.⁶ .................................................. A61F 2/04
[52] U.S. Cl. .................................................. 623/12; 623/1
[58] Field of Search ..................... 623/1, 12, 11; 606/191

[56] References Cited

U.S. PATENT DOCUMENTS

| | | | |
|---|---|---|---|
| 1,920,495 | 8/1933 | Brown et al. | 140/7 |
| 2,836,181 | 5/1958 | Tapp | 128/334 |
| 2,997,839 | 4/1961 | Koch | 87/1 |
| 3,095,017 | 6/1963 | Bleiler et al. | 139/387 |
| 3,105,492 | 10/1963 | Jeckel | 128/334 |
| 3,272,204 | 9/1966 | Artandi et al. | 128/334 |
| 3,304,557 | 2/1967 | Polansky | 3/1 |
| 3,317,924 | 5/1967 | Le Veen et al. | 3/1 |
| 3,463,158 | 8/1969 | Schmitt et al. | 128/334 |
| 3,479,670 | 11/1969 | Medell | 3/1 |
| 3,485,234 | 12/1969 | Stevens | 128/2 |
| 3,509,883 | 5/1970 | Deibelius | 128/348 |
| 3,526,906 | 9/1970 | De Laszlo | 3/1 |
| 3,562,820 | 2/1971 | Braun | 3/1 |
| 3,580,289 | 5/1971 | James, Jr. | 138/121 |
| 3,585,707 | 6/1971 | Stevens | 29/427 |
| 3,626,947 | 12/1971 | Sparks | 128/334 R |
| 3,710,777 | 1/1973 | Sparks | 128/1 R |
| 3,730,835 | 5/1973 | Leeper | 195/1.7 |
| 3,822,238 | 7/1974 | Blair et al. | 260/75 |
| 3,868,956 | 3/1975 | Alfidi et al. | 128/345 |
| 3,878,565 | 4/1975 | Sauvage | 3/1 |
| 3,929,126 | 12/1975 | Corsaut | 128/240 |

(List continued on next page.)

FOREIGN PATENT DOCUMENTS

| | | |
|---|---|---|
| 0 587 197 | 10/1991 | European Pat. Off. |
| 1 602 513 | 1/1970 | France . |
| 30 19 996 | 12/1981 | Germany . |
| 1 205 743 | 9/1970 | United Kingdom . |
| 2 015 118 | 9/1979 | United Kingdom . |
| 2 033 233 | 5/1980 | United Kingdom . |
| 2 077 107 | 12/1981 | United Kingdom . |
| 2 135 585 | 3/1986 | United Kingdom . |
| WO88/00813 | 2/1988 | WIPO . |
| WO91/12779 | 9/1991 | WIPO . |
| WO94/24961 | 11/1994 | WIPO . |

OTHER PUBLICATIONS

"A Study of the Geometrical and Mechanical Properties of a Self–Expanding Metallic Stent . . . " Jedwab et al, Jour. of Applied Biomaterials, Vo. 4, pp. 77–85 1993.

"Oesophageal Strictures" Didcott, Annals of the Royal Cllege of Surgeons of England, vol. 55, pp. 112–126, Aug. 1973.

*Primary Examiner*—Michael J. Milano
*Attorney, Agent, or Firm*—David P. Gordon

[57] ABSTRACT

A self-expanding stent is provided for introduction into a cavity of a human body. The stent has a tubular body which is radially expansible and axially retractable between a working state and a resting state. The tubular body has first and second plaited filaments which provide a middle portion of a first diameter and two flared end portions of increasingly larger diameter as they extend away from the middle portion. Each flared end portion has an axial length along a longitudinal axis of the stent which is greater than an axial length of the portion of minimal diameter. Preferably, the middle portion is a single location, with the diameter of the stent increasing in both directions from that location to the ends of the stent. Different shaped stents are disclosed, including stents having generatrices taking the form of line segments angled relative to the longitudinal axis, and generatrices taking the form of a hyperbola segment or a circle arc segment.

20 Claims, 3 Drawing Sheets

U.S. PATENT DOCUMENTS

| | | | |
|---|---|---|---|
| 3,974,526 | 8/1976 | Dardik et al. | 3/1.4 |
| 3,993,078 | 11/1976 | Bergentz et al. | 128/334 R |
| 4,044,404 | 8/1977 | Martin et al. | 3/19 |
| 4,086,665 | 5/1978 | Poirier | 3/1.4 |
| 4,106,129 | 8/1978 | Carpentier et al. | 3/1.5 |
| 4,130,904 | 12/1978 | Whalen | 3/1.4 |
| 4,134,402 | 1/1979 | Mahurkar | 128/214 R |
| 4,140,126 | 2/1979 | Choudhury | 128/325 |
| 4,164,045 | 8/1979 | Bokros et al. | 3/1.4 |
| 4,173,689 | 11/1979 | Lyman et al. | 521/64 |
| 4,193,138 | 3/1980 | Okita | 3/1.4 |
| 4,323,071 | 4/1982 | Simpson et al. | 128/343 |
| 4,355,426 | 10/1982 | MacGregor | 3/1.4 |
| 4,441,215 | 4/1984 | Kaster | 3/1.4 |
| 4,459,252 | 7/1984 | MacGregor | 264/46.9 |
| 4,475,972 | 10/1984 | Wong | 156/167 |
| 4,503,569 | 3/1985 | Dotter | 3/1.4 |
| 4,583,968 | 4/1986 | Mahurkar | 604/43 |
| 4,610,688 | 9/1986 | Silvestrini et al. | 623/1 |
| 4,655,771 | 4/1987 | Wallsten | 623/1 |
| 4,692,141 | 9/1987 | Mahurkar | 604/43 |
| 4,731,073 | 3/1988 | Robinson | 623/1 |
| 4,743,251 | 5/1988 | Barra | 623/1 |
| 4,787,899 | 11/1988 | Lazarus | 623/1 |
| 4,850,999 | 7/1989 | Planck | 623/1 |
| 4,871,357 | 10/1989 | Hsu | 604/266 |
| 4,875,480 | 10/1989 | Imbert | 128/343 |
| 4,878,906 | 11/1989 | Lindemann et al. | 623/4 |
| 4,895,561 | 1/1990 | Mahurkar | 604/43 |
| 4,935,006 | 6/1990 | Hasson | 604/43 |
| 4,954,126 | 9/1990 | Wallsten | 606/36 |
| 5,015,253 | 5/1991 | MacGregor | 623/1 |
| 5,026,377 | 6/1991 | Burton et al. | 606/108 |
| 5,061,275 | 10/1991 | Wallsten et al. | 623/1 |
| 5,064,435 | 11/1991 | Porter | 623/12 |
| 5,078,720 | 1/1992 | Burton et al. | 606/108 |
| 5,116,360 | 5/1992 | Pinchuk et al. | 623/1 |
| 5,123,917 | 6/1992 | Lee | 623/11 |
| 5,160,341 | 11/1992 | Brenneman et al. | 606/198 |
| 5,188,593 | 2/1993 | Martin | 604/43 |
| 5,197,978 | 3/1993 | Hess | 623/1 |
| 5,201,757 | 4/1993 | Heyn et al. | 606/198 |
| 5,235,966 | 8/1993 | Jamner | 128/20 |
| 5,242,399 | 9/1993 | Lau et al. | 604/104 |
| 5,279,561 | 1/1994 | Roucher et al. | 604/96 |
| 5,290,295 | 3/1994 | Querals et al. | 606/108 |
| 5,312,415 | 5/1994 | Palermo | 606/108 |
| 5,330,500 | 7/1994 | Song | 606/198 |
| 5,360,397 | 11/1994 | Pinchuk | 604/27 |
| 5,382,259 | 1/1995 | Phelps | 623/1 |
| 5,383,892 | 1/1995 | Cardon et al. | 606/198 |
| 5,395,390 | 3/1995 | Simon et al. | 606/198 |
| 5,397,355 | 3/1995 | Marin et al. | 623/12 |
| 5,405,378 | 4/1995 | Strecker | 623/1 |
| 5,415,664 | 5/1995 | Pinchuk | 606/108 |
| 5,433,723 | 7/1995 | Lindenberg et al. | 606/198 |
| 5,503,636 | 4/1996 | Schmitt | 623/12 |
| 5,545,208 | 8/1996 | Wolff | 623/1 |
| 5,618,301 | 4/1997 | Hauenstein | 623/1 |

5,741,333

SELF-EXPANDING STENT FOR A MEDICAL DEVICE TO BE INTRODUCED INTO A CAVITY OF A BODY

This application claims priority from Belgium Application Number 9500334, filed Apr. 12, 1995, the complete disclosure of which is hereby incorporated by reference herein in its entirety. This application is also related to co-owned U.S. application Ser. No. 08/626,932, filed Apr. 3, 1996, the complete disclosure of which is hereby incorporated by reference herein in its entirety.

BACKGROUND OF THE INVENTION

1. Field of the Invention

The present invention relates to a self-expandable stent for a medical device to be introduced into a cavity of a human or animal body. More particularly, the present invention relates to a stent having a tubular body which is radially expandable and axially retractable between a working state of the stent and a resting state of the stent, and is axially expandable and radially retractable between the resting state of the stent and its working state, this tubular body comprising first flexible rigid filaments wound along a first direction around a longitudinal axis of the tubular body, and second flexible rigid filaments wound along a second direction, opposite to the first, around the longitudinal axis, each filament wound in one of the said directions crossing filaments wound in the other direction according to a woven or braided arrangement. The term "self-expanding stent" is intended according to the invention to mean that, when brought into its working position, that is to say a radially compressed and axially extended position, the stent, once released, tends spontaneously to recover to approximately its resting position, that is to say a radially expanded and axially contracted position. Also, for purposes herein, the term "medical device to be introduced into a cavity of a human or animal body" should be taken to mean, for example, luminal endoprostheses, catheters, dilators, grafts and the like which can be introduced, for example, into the vascular, esophageal, urinary, urethral, biliary cavities and other tubular ducts of the body as well as in man-made ducts or passages such as those used in transjugular intrahepatic portalsystemic shunts (TIPS). Further, the terms "woven", "braided", and "plaited" are used interchangeably herein and are intended to be understood in their broadest sense to require an over-under interlacing of a plurality of filaments.

2. State of the Art

Self-expanding stents which are used as vascular, esophageal or other dilators have been known for a long time (See, e.g., GB1,205,743). These stents, formed by a tubular plaited structure of individual filaments include, in the resting state, filaments forming a fairly small angle (e.g., 30°) with respect to a longitudinal axis of the tube. Stents of this type do not offer a sufficient capacity for radial expansion when they are released after having been radially compressed. Their crushing resistance is also insufficient when they are used in cavities of the body whose walls exert a strong radial pressure on the stent introduced.

It has consequently been sought to overcome these drawbacks by providing a woven structure of individual filaments with a larger angle so that, in the resting state of the stent, the filaments exhibit an angle greater than 45°, preferably of at least 60° with respect to the longitudinal axis of the stent (See, e.g., U.S. Pat. No. 4,655,711 and U.S. Pat. No. 4,954,126). However, stents with a large plaiting angle have a great drawback. Indeed, the tubular stent must be extended to two to three times its initial length in order to be capable of being inserted in a vascular introducer. It then occupies from 40 to 50% of the length of the introducer, stiffening it and making it difficult to pass through the femoral artery through which introduction into the body is generally initiated. On release, the tubular structure retracts by two to three times in length. It is therefore very difficult to estimate the length which will be deployed in the internal cavity of the body treated, and the exact location where the stent will be anchored, both of which may lead to serious problems. For example, a length of stent may be deployed beyond a vascular bifurcation and thus lead to undesirable artery closure when the stent is provided with a covering, as is the case for luminal endoprostheses. In another case, if the deployed length is too short, the aneurysm treated will not be closed. Finally, it has been observed that stents with a large plaiting angle formed by individual filaments did not exhibit good resistance to blood pressure inside the aneurysms treated. Inside the aneurysm, that is to say where the stents do not undergo radial compression by the vascular wall, they tend to balloon, which promotes losses of leak-tightness.

Other filament-based tubular plaited structures, which are used in devices to be introduced into the human body, are also described, in particular, in EP-A-0,183,372, U.S. Pat. No. 3,509,883, U.S. Pat. No. 5,061,275 and U.S. Pat. No. 5,171,267. In Patent U.S. Pat. No. 5,061,275, in particular, the possibility has been provided of making braided tubular bodies whose ends flare conically with respect to the rest of the body, which is of a cylindrical shape. Without solving the aforementioned problem of ballooning in the aneurysms, this embodiment of the stent allows only slight adaptation of the length to the case to be treated. As soon as the surgeon cuts an excessive length from one end, for example, of an endoprosthesis fitted with such a stent, this end no longer exhibits flaring and has lost the advantage that the flaring provides.

SUMMARY OF THE INVENTION

In order to solve the problems raised herein above, a self-expanding stent is provided according to a first embodiment of the present invention, where the tubular body assumes substantially the form of a hyperboloid in the resting state; i.e., the tubular body can be defined by a generatrix in the form of a hyperbola rotated about the longitudinal axis of the stent. In other words, the stent has two flared ends of large diameter which extend from a center portion or location of smaller diameter. Preferably, the hyperboloid-shaped stent is arranged such that the diameter of the cross section of the stent decreases continuously from the ends to the point of smallest diameter. By virtue of this substantially hyperboloid arrangement, the stent opposes any ballooning inside an aneurysm while retaining its good properties of attachment by its flared ends on release in a tubular cavity of a human or animal body. This is still true if the surgeon has reduced a part of the length of the stent by cutting, as the new end formed still remains flared with respect to the rest of the stent. Finally, the radial expansion of the flared parts of the stent is maintained on release, and the flared parts, by conforming well to the shapes of the vascular walls in which they are released, efficiently prevent migration of the stent along these walls.

Different braiding or weaving arrangements of the filaments of the substantially hyperboloid stent can be utilized. In one embodiment, a first filament will, when crossing over with a second filament, pass above the latter and, during the subsequent cross-over, pass below the second filament then crossed, and so on. In another embodiment, the first filament passes above a second filament during two or more successive cross-overs and will then only pass below a second filament after this plurality of successive cross-overs, and so on. Mixed plaited arrangements may also be provided. The plaited structures according to the invention may be formed completely by monofilaments, as in the prior art.

According to an advantageous form of the invention, the filaments may be arranged as multiple filaments: for example double or triple filaments or more. Monofilaments may be used in conjunction with the multiple filaments. The term multiple filaments is intended to mean filaments arranged adjacently side by side in a number at least equal to two, which are wound around the axis of the tubular body of the stent. The embodiments with plaited multiple filaments have the greater advantage of excellent dimensional and geometrical stability, without requiring a large plaiting angle, and the accuracy on release of such stents is therefore greatly increased.

According to another embodiment of the invention, the flared ends of the tubular body form frustoconical portions which extend from the center portion of the tubular member; i.e., the tubular body is defined by two generatrices which are lines angled relative to the longitudinal axis of the stent. Preferably, the cross-sectional diameter of the stent increases continuously in each direction away from a center portion of the stent. According to a further embodiment of the invention, the tubular body of the stent is defined by a generatrix in the shape of a circle arc.

According to another advantageous embodiment of the invention, a stent-graft is provided with an expandable covering applied to at least one of an external wall surface and an internal wall surface of the stent body. Such a covering may be applied onto the stent using any known technique; for example in accordance with the teaching of EP-A-0.603,959. This makes it possible to form, for example, luminal prostheses having an at rest diameter of 55–60 mm at the ends and 25–30 mm at the center, the covering of which is made of polycarbonate-urethane or other fibers with a fiber diameter of 5–25 μm. The diameters of such endoprostheses may then be reduced to a diameter of 4 to 5 mm for insertion in an introducer. The graft covering may take many forms and may be produced using any of many other techniques such as phase inversion, particle elution, spray techniques with volatile solvents, replamineform techniques, or other techniques without departing from the scope of the invention.

The invention will now be described in more detail in the following description of non-limiting embodiments and with reference to the attached drawings.

DETAILED DESCRIPTION OF THE PREFERRED EMBODIMENTS

Figure 1:
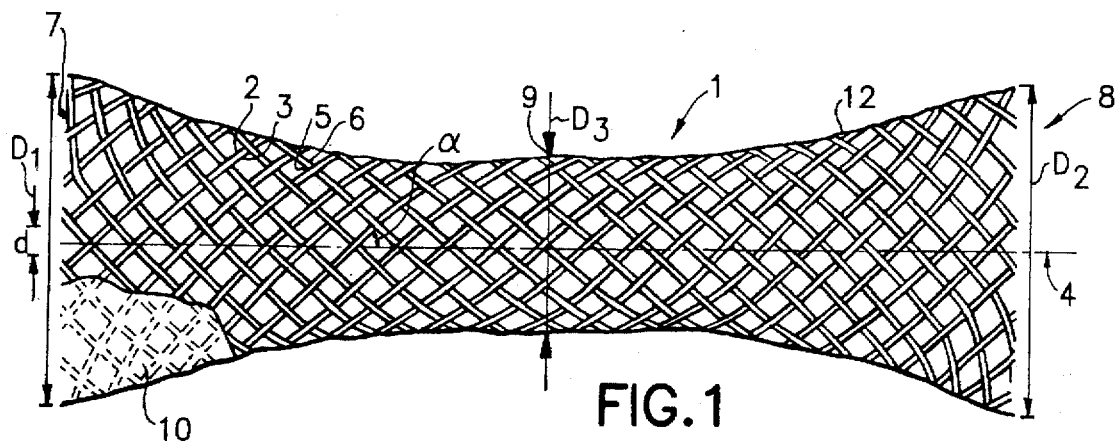
FIG. 1 represents a partially cut away side view of one embodiment of a self-expanding stent according to the invention.

As can be seen from FIG. 1, the self-expanding stent according to the invention is formed by a tubular body 1 having, in this example, a hyperboloid shape. The tubular body 1 is formed by braided filaments. It comprises first filaments, for example 2 and 3, which are arranged side by side, there being two of them in this case, and which thus form first multiple filaments wound along a first direction around the longitudinal axis 4 of the tubular body. It also comprises second filaments 5 and 6 which are arranged side by side, there being two of them in this case, and which thus form second multiple filaments wound along a second direction, opposite to the first, around the aforementioned longitudinal axis 4. It is clear that three, four or more filaments may be provided, arranged side by side, in order to form a multiple filament according to the invention. It should also be noted that the filaments arranged side by side to form a multiple filament are contiguous over almost their entire length. It is only for reasons of clarity and readability that the filaments forming a multiple filament, such as the filaments 2 and 3 or 5 and 6, respectively, in FIG. 1, are represented slightly separated from each other.

As can be seen in FIG. 1, the multiple filaments of the tubular body 1 cross according to a braided arrangement, it being possible to vary the mode of plaiting as already indicated above.

The multiple filaments used consist of any material which is suitable for introduction into the human and animal body and which has sufficient rigidity and flexibility to produce an self-expanding stent. Biocompatible metallic filaments may be provided. Such filaments may be formed from, for example, stainless steel, wrought cobalt chromium nickel alloys satisfying standards ISO 5832/7 and/or ASTM F1058-91, ELIGLOY, NITINOL, or PHYNOX with AFNOR designation K13 C20 N16 Fe15 Do7, marketed by Sprint Metal, Paris, France. It is clear that other metallic filaments or filaments of other materials, for example of plastics having elastic memory, may be used.

In FIG. 1, a first embodiment of the tubular body 1 is represented in the resting state. In this state it has a first flared end 7 of diameter $D_1$ and a second flared end 8 of diameter $D_2$ which can be equal or not equal to $D_1$. Between these two flared ends there is a center location 9 of the tubular body having a diameter $D_3$ which is less than $D_1$ and $D_2$. By way of example, the diameter $D_3$ may be approximately 28 mm, and the diameters $D_1$ and $D_2$ may be approximately 58 mm. Between each flared end 7 or 8 and the location 9 of smallest cross-sectional diameter, the tubular body 1 has a cross-sectional diameter which decreases continuously. In the case illustrated, this decrease is such that the tubular body includes a generatrix 12 in the shape of a hyperbola such that the tubular body assumes the shape of a hyperboloid. In its compressed state, that is to say at the time when it will be required to be introduced in a known introducer (not shown), the stent will need to have a diameter d which may be as small as 3 to 5 mm. The compressed state is obtained by radial compression of the stent and/or by moving apart the ends of the stent in the axial direction. In the compressed state, the stent therefore has a length greater than its length in the resting state.

In the resting state the filaments of stent 1 have, with respect to the longitudinal axis 4 of the stent, an angle α which varies continuously. At the central part of the stent, this angle is preferably at most 45° and advantageously less than 45°. At the flared ends the directed angle is clearly much larger. This offers the great advantage that the stent, in the working state, when inserted in its introducer, does not have an excessive length with all the release problems associated therewith, as already indicated above. Moreover, the radial expansion of the ends is excellent and allows good attachment of the stent to a vessel, thereby preventing the stent from migrating during or after release and providing good leaktightness.

As can be seen in FIG. 1, the tubular body 1 may be lined on its internal surface with a covering 10. This covering may be made of any biocompatible material which is suitable, in particular, for the manufacture of luminal endoprostheses (see EP-A-0,603,959). A covering on the external surface may be provided instead of or in addition to the internal covering 10.

Figure 2:
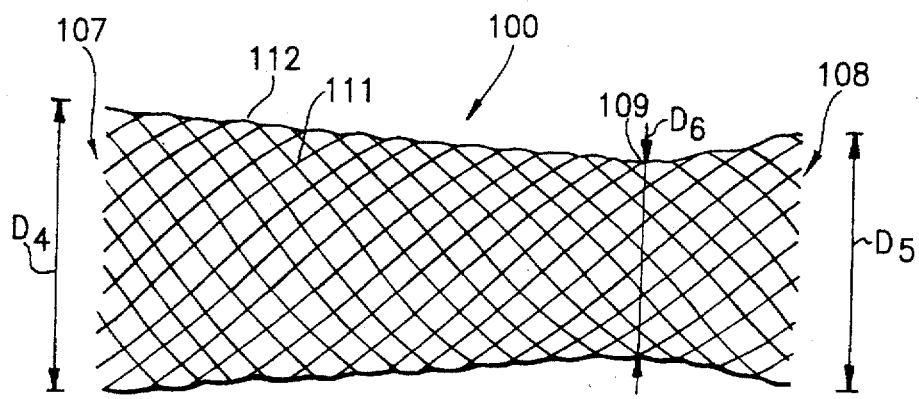
FIG. 2. represents a side view of a second embodiment of stent according to the invention.

FIG. 2 illustrates a stent according to another embodiment of the invention with a tubular body 100 having a first flared end 107 of diameter $D_4$ and a second end 108 of diameter $D_5$ less than $D_4$. A location 109 of minimum cross-sectional diameter $D_6$ located at a shorter distance from the end 108 than from the end 107, which gives rise to a tubular body of asymmetric shape. Between each flared end 107 or 108 and the location 109 of smallest cross-sectional diameter, the tubular body forms a frustoconical shape (i.e., the body is defined by a generatrix 112 on each side which is in the shape of a straight line angled relative to the longitudinal axis). As can be seen, in this embodiment, the plaited filaments are individual filaments or monofilaments 111 which follow a helix with radii which increase as they extend away from location 109.

Figure 3:
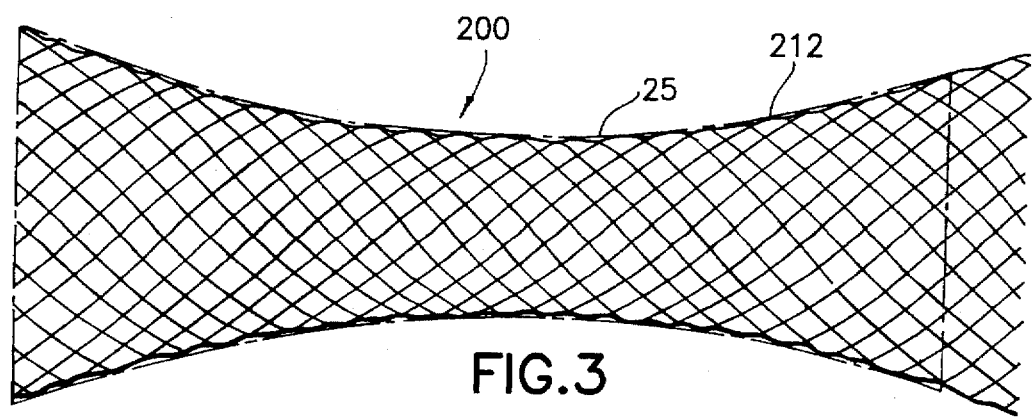
FIG. 3 represents a side view of a third embodiment of a stent according to the invention.

FIG. 3 illustrates a stent where the tubular body 200 is defined by a generatrix 212 in the shape of a circle arc.

It is clear that other stents within the scope of the invention may be generated using other generatrices such as a segment of an ellipse, oval, hypocycloid, parabola and of similar curves which are rotated about the longitudinal axis of the stent.

It should be understood that the generatrices on either side of the location of smallest cross-sectional diameter may be of different types and sizes.

The embodiments according to the invention offer the great advantage of allowing good fixing of the stent during release, without subsequent migration in the cavity. Attachment to the wall of this cavity takes place much more intensely at the end which is released first, by virtue of its flared shape, and this end keeps the released device in the position which was given to it. A stent according to the invention proves highly advantageous, in particular when introducing an endoprosthesis for treating an abdominal artery aneurysm. Its two ends match the shape of the necks of the aneurysm while thus perfectly retaining the endoprosthesis which is at this location subjected to the stresses due to blood pressure. The central part of the stent, bent inwards and having a restoring force in this direction, perfectly resists this blood pressure in the aneurysm, where radial compression is no longer exerted on the stent by the vascular walls.

The stents according to the invention are also very well suited to treating subclavian artery aneurysms, in which the stent may be greatly bent at one end. Instead of being crushed by closing up at this end, as is typical of the cylindrical stents of the prior art, the stent remains in a largely open position at its end, by virtue of the shape of the latter. A cutting of the stent by the surgeon for giving it the correct length presents no risk because the flared shape at the ends remains in spite of this cutting. With the stents of the invention, there is therefore no longer any need to store multiple endoprostheses with different lengths.

Figure 4:
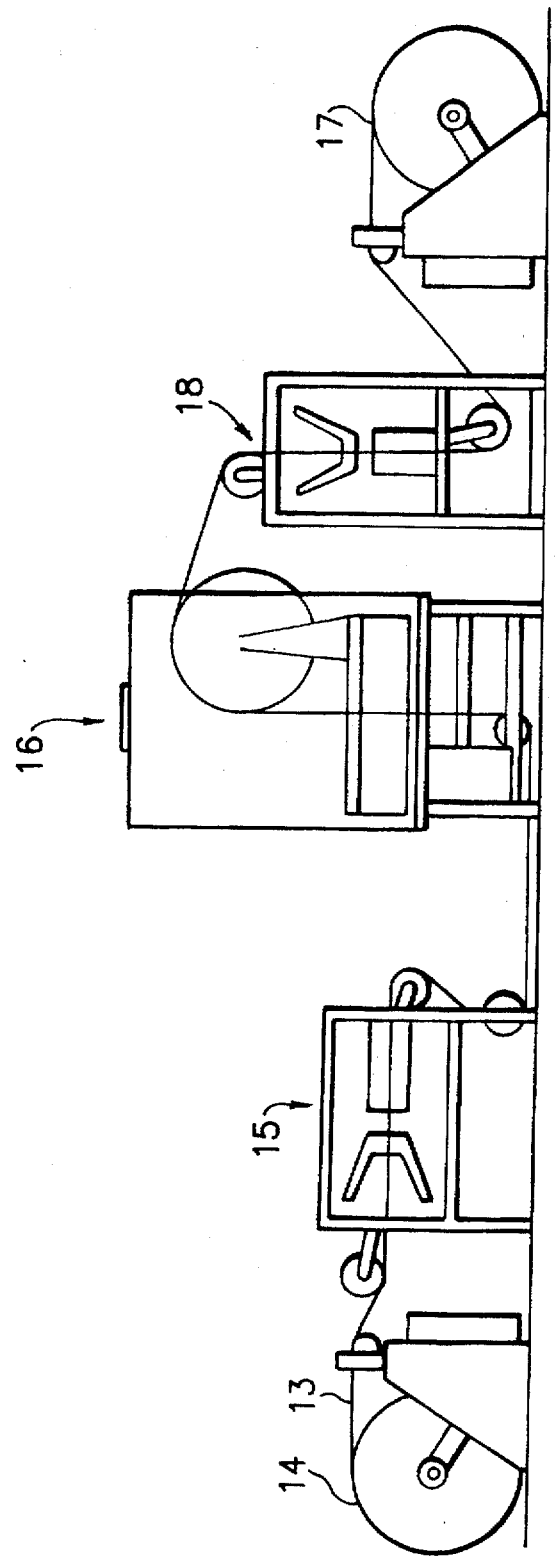
FIG. 4 represents a general diagram of the plaiting equipment for making the stent in accord with the invention.
Figure 5:
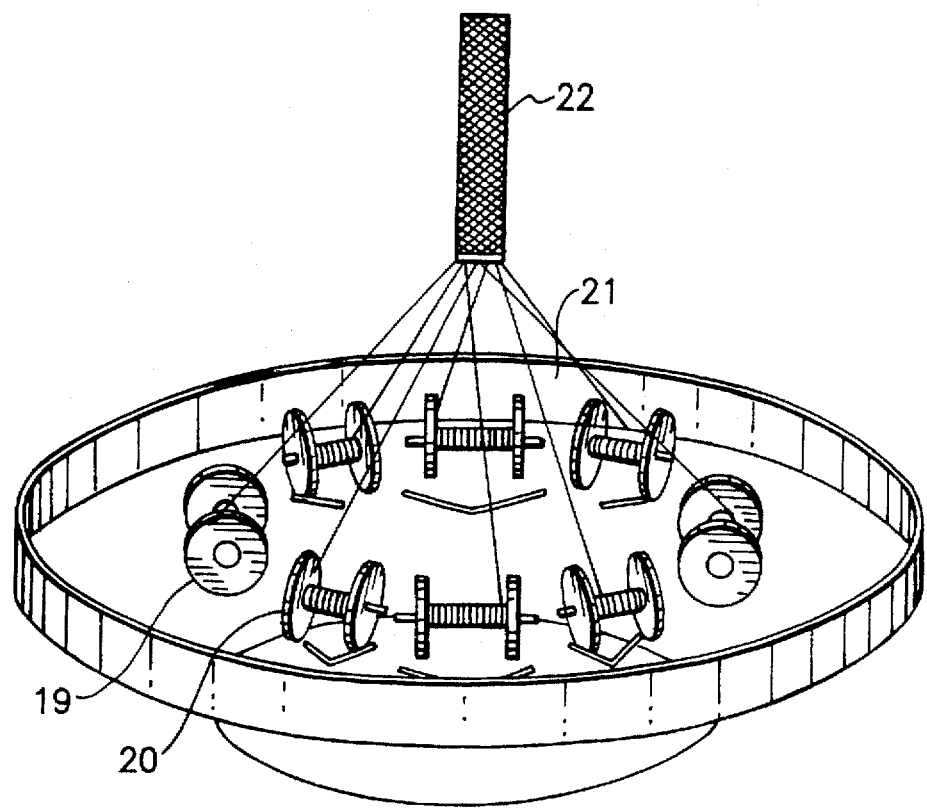
FIG. 5 represents a more detailed view of the plaiting operation.

The manufacture of a plaited tubular body has been known for a long time in the technique of cable production, and use is made here of the technique which is illustrated in the attached FIGS. 4 and 5. In FIG. 4, a bearing cable 13 is unwound from a spool 14. A guidance system, denoted overall by the reference 15, guides and tensions this cable 13 which passes through the plaiting machine 16 schematized here. It leaves this machine, provided with a plaited tubular body and is then wound onto a spool 17 after having been tensioned by a new guidance system 18.

The exemplary plaiting machine 16 used is represented in somewhat more detail in FIG. 5. As a plaiting machine of this type, use may, for example, be made of a DBH or DB model machine Meximieux, France, or a Wardwell-type (deflecting wire type) machine where the wires are deflected up and over the spool, or a Butt-type braider having a shuttling spool. The reels of the machine of FIG. 5 (only some of which have been represented) are divided into two groups, with the reels 19 of one group rotating in the opposite direction to the reels 20 of the other group, about the axis of the plaited structure. The bearing cable or braiding mandril passes through the middle of the plaited structure.

According to the invention, single or multiple filaments 21, also generally referred to as "multiple ends", are unwound from reels. Moreover, prior to braiding, a plurality of filaments may have been simultaneously wound onto some or all of the reels. As already stated, these multiple filaments originating from the reels are contiguous over almost their entire length, and this is why they are not seen individually in FIG. 5. The choice of the number of reels depends on the diameter of the desired plaited structure 22.

Figure 6:
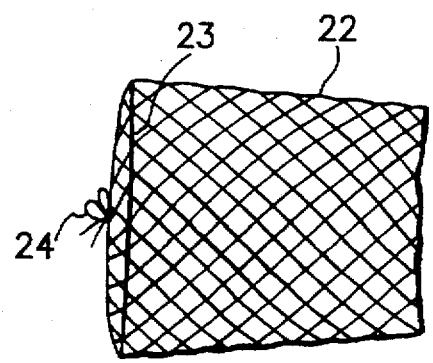
FIG. 6 represents a partial view of a stent according to the invention at the end of manufacture.

Advantageously, in the resting state, the plaited cylindrical tubular body has, after plaiting, a diameter slightly greater than the diameter of the location of smallest cross-sectional diameter of the finished stent. The plaited tubular body is then removed from its bearing cable or from the braiding mandrel, and in a conventional manner, the plaited tubular body can then be placed over a mandrel. However, according to the invention, this mandrel, denoted by reference number 23 and partially represented in FIG. 6, has the appropriate desired shape with a cross-section with a continuously variable diameter. The plaited tubular body 22 is then secured at 24 at one end, then at the other, which subjects it to tension. The plaited tubular body then matches the external shape of the mandrel 23 and it is then subjected to a thermal setting treatment which fixes the tubular body at the dimensions of the mandrel. For example, a tubular plaited structure with a smallest diameter of 35 mm may be knotted onto a mandrel as described, having a central diameter of 28 mm. The filament undergoes setting, for example, at 550° C. for three hours, under an inert atmosphere (argon or nitrogen with 5% hydrogen) or under a vacuum of $10^{-4}$ to $10^{-8}$ torrs. Following this treatment, the finished stent has a shape according to the invention which corresponds, for example, to one of those represented in FIGS. 1 to 3.

According to the invention, provision is also made, as a variant, to extend the plaited tubular body and introduce it in a tube 25, represented in dots and dashes in FIG. 3, which is defined by a angled or curved generatrix such that the tube increases in diameter continuously from a location of smallest diameter to the ends of larger diameter. The tubular body thus introduced is then subjected to the thermal setting treatment. Following this treatment, if the plaited structure has been completely introduced in the tube 25, the finished stent has a shape corresponding to that of the internal cavity of the tube. Provision may also be made, as represented on the right side of FIG. 3, for at least one of the two ends of the plaited structure to protrude from the tube before setting.

The great advantage of thermally setting stents in tubes is that the finished stents obtain an angular arrangement of the filaments which is, under the same treatment conditions, always perfectly reproducible. This is in contrast to the prior art situation where the setting is accomplished on a mandrel.

It should be understood that the present invention is in no way limited to the forms and embodiments described hereinabove. For example, it should be appreciated that while the stents of the invention have been described as continuously varying in diameter, if desired, a small middle portion can be provided of constant diameter, provided the axial length of that middle portion is smaller relative to the axial lengths of the flaring portions. Therefore, it will be appreciated that other modifications may certainly be made to the invention without departing from the spirit and scope of the appended claims.

I claim:

1. A self-expanding stent for introduction into a cavity of a human or animal body, comprising:

a tubular body which is radially expandable and axially retractable between a compressed state and a resting state, and is axially expandable and radially retractable between said resting state and said compressed state, and having first filaments having elastic memory wound along a first direction around a longitudinal axis of said tubular body, and second filaments having elastic memory wound along a second direction, opposite to said first direction, around said longitudinal axis, each filament wound in one of said directions crossing filaments wound in the other direction according to a plaited arrangement, wherein, in said resting state prior to introduction into a cavity, said tubular body includes a middle portion of a first diameter and two flared end portions starting with said first diameter and of increasingly larger diameter as they extend away from said middle portion, wherein each of said flared end portions has an axial length along said longitudinal axis greater than an axial length of said middle portion.

2. A self-expanding stent according to claim 1, wherein: said middle portion is substantially a location on said stent, and said tubular body has a diameter which increases continuously from said location to a first end of said stent and from said location to a second end of said stent.

3. A self-expanding stent according to claim 1, wherein: said stent has first and second ends, and between each of said ends and said middle portion said tubular body is defined by a generatrix in the shape of a straight line.

4. A self-expanding stent according to claim 1, wherein: said stent has first and second ends, and between each of said ends and said middle portion said tubular body is defined by a generatrix in the shape of a curved segment.

5. A self-expanding stent according to claim 4, wherein: said curved segment is a hyperbola.

6. A self-expanding stent according to claim 4, wherein: said curved segment is a circle arc.

7. A self-expanding stent according to claim 2, wherein: a portion between each of said first and second ends of said stent and said middle portion is defined by a generatrix in the shape of a straight line.

8. A self-expanding stent according to claim 2, wherein: a portion between each of said first and second ends of said stent and said middle portion is defined by a generatrix in the shape of a curved segment.

9. A self-expanding stent according to claim 2, wherein: said location is located half-way between said first and second ends.

10. A self-expanding stent according to claim 2, wherein: said location is located a shorter distance from said first end than from said second end.

11. A self-expanding stent according to claim 1, wherein: said stent has a first end having a second diameter, and a second end having a third diameter, and said third diameter is larger than said second diameter.

12. A self-expanding stent according to claim 1, wherein: said stent has a first end having a second diameter, and a second end having a third diameter, and said third diameter is equal to said second diameter.

13. A self-expanding stent according to claim 1, wherein: each of said first filaments and each of said second filaments are individually wound filaments.

14. A self-expanding stent according to claim 1, wherein: a plurality of said first filaments are arranged side by side in a number at least equal to two and thus form first multiple filaments.

15. A self-expanding stent according to claim 1, further comprising:

an expandable covering located on one of an internal surface and an external surface of said tubular body.

16. A self-expanding stent according to claim 1, wherein: said filaments are metal filaments.

17. A method for preparing an self-expanding stent for introduction into a cavity of a body, comprising:

a) plaiting filaments originating from interposed reels rotating in opposite directions so as to form a plaited stent which is radially expansible and retractable between a working state and a resting state of the stent, and is axially expansible and retractable between said working state and said resting state, and having a location of minimum first diameter;

b) providing a tube having an internal cavity having a middle portion of a second diameter smaller than said minimum first diameter, and two flared end portions starting with said second diameter and of increasingly larger diameter as they extend away from said middle portion, wherein each of said flared end portions has an axial length along a longitudinal axis of said tube greater than an axial length of said portion of minimum first diameter;

c) axially expanding said plaited stent and introducing it into said tube;

d) thermally treating, setting, and fixing said stent while in said tube in order to fix said stent so that in said resting state, said stent has a shape corresponding to that of said internal cavity of said tube.

18. A method according to claim 17, wherein: after said introducing said stent into said tube, at least one of a first end and a second end of said stent protrudes and flares from said tube.

19. A method according to claim 17, further comprising: prior to said plaiting, winding at least some of the interposed reels with multiple filaments arranged side by side.

20. A self-expanding stent for introduction into a cavity of a human or animal body, comprising:

a tubular body which is radially expandable and axially retractable between a compressed state and a resting state, and is axially expandable and radially retractable between said resting state and said compressed state, said tubular body having two flared end portions having ends of different diameter.

* * * * *